US00PP21226P2

(12) United States Plant Patent

Hoekstra-Arisz

(10) Patent No.: US PP21,226 P2

(45) Date of Patent: Aug. 24, 2010

(54) *SYMPHORICARPOS* PLANT NAMED 'SOFIE'

(50) Latin Name: ***Symphoricarpos* hybrid**
Varietal Denomination: Sofie

(76) Inventor: Catharina Marie Hoekstra-Arisz, Creutzberglaan 10, Beverwijk (NL) 1943

( * ) Notice: Subject to any disclaimer, the term of this patent is extended or adjusted under 35 U.S.C. 154(b) by 0 days.

(21) Appl. No.: 12/380,500

(22) Filed: Feb. 27, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Susan B McCormick Ewoldt

(57) ABSTRACT

A new and distinct *Symphoricarpos* hybrid cultivar named 'SOFIE' is disclosed, characterized by large berries, long fruiting stems, light green foliage and pink berries tinged with white. The new variety is a *Symphoricarpos* hybrid, suitable for outdoor landscape and decorative cut fruiting stem use.

2 Drawing Sheets

Latin name of the genus and species: *Symphoricarpos* hybrid.

Variety denomination: 'SOFIE'.

BACKGROUND OF THE INVENTION

The new cultivar is a chance seedling selection by the inventor, Catharina Maria Hoekstra-Arisz, a citizen of the Netherlands. The new variety was discovered at a commercial nursery in Beverwijk, The Netherlands, in October 2003, by the inventor growing in the ground among a field of mixed commercial varieties of *Symphoricarpos*. The parent varieties are unknown.

Asexual reproduction of the new cultivar 'SOFIE' by vegetative cuttings was first performed in March 2006, at a commercial nursery in Beverwijk, The Netherlands and has shown that the unique features of this cultivar are stable and reproduced true to type in successive generations.

SUMMARY OF THE INVENTION

The cultivar 'SOFIE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SOFIE' These characteristics in combination distinguish 'SOFIE' as a new and distinct *Symphoricarpos* cultivar:

1. Large berries.
2. Long fruiting stems.
3. Light green foliage.
4. Pink berries tinged with white.

COMMERCIAL COMPARISION

Plants of the new cultivar 'SOFIE' are similar to plants of the unpatented variety, *Symphoricarpos* hybrid 'Purple Hedge' in most horticultural characteristics, however, plants of the new cultivar have lighter foliage, longer stems, and lighter colored, larger berries.

BRIEF DESCRIPTION OF THE PHOTOGRAPH

Figure 1:
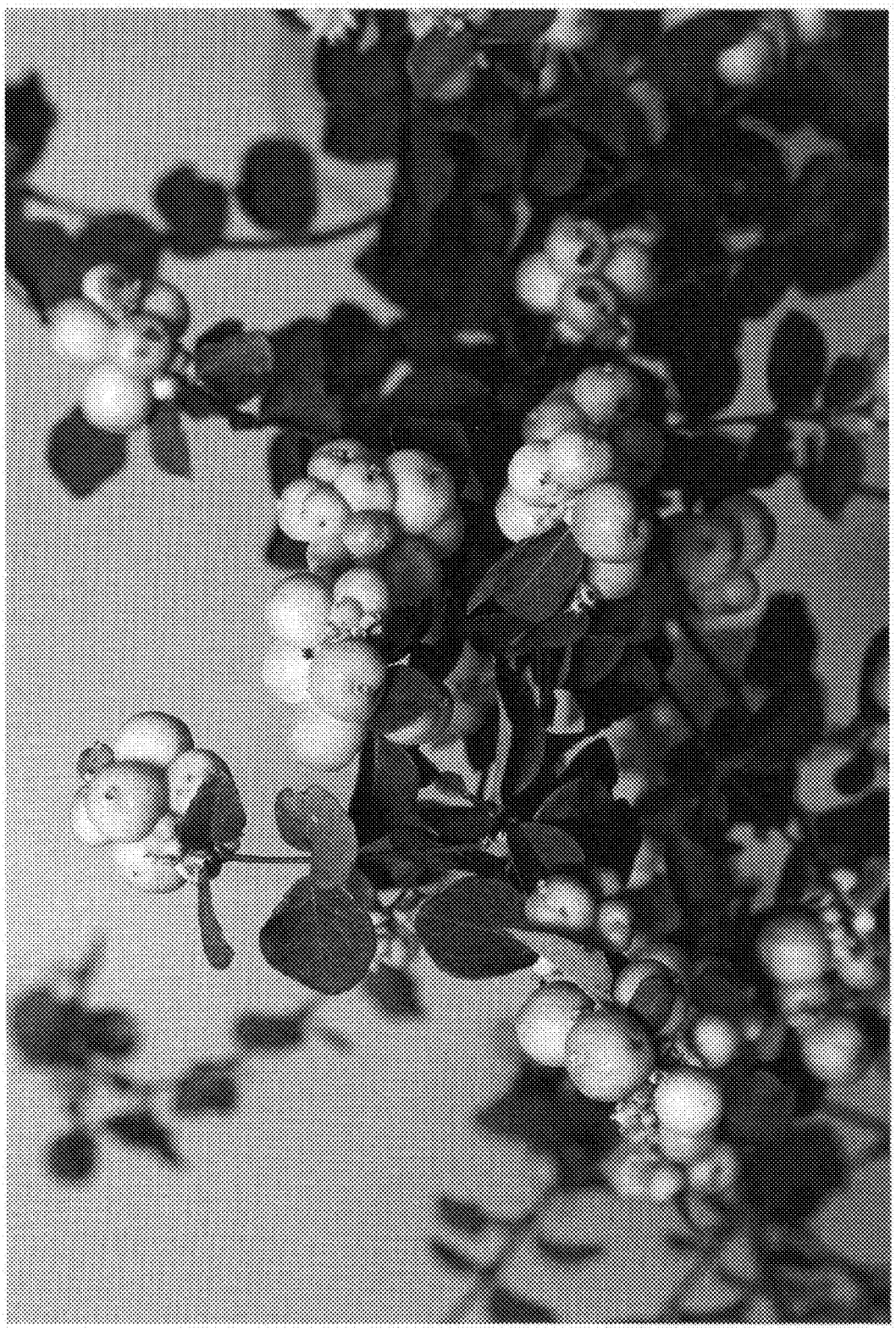

The accompanying photograph in FIG. 1 illustrates in full color a close up of the berries produced by 'SOFIE.'

Figure 2:
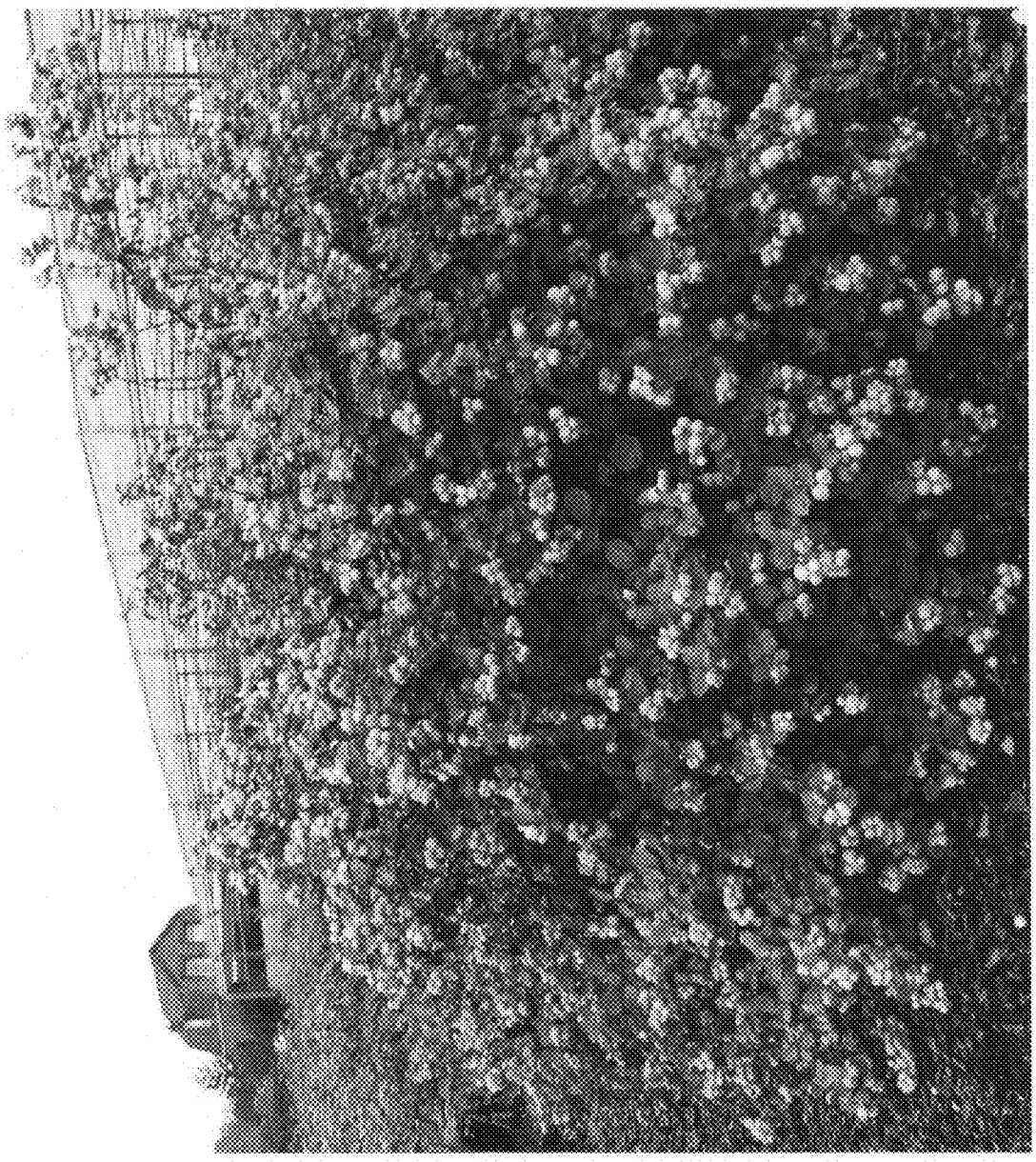

The photograph in FIG. 2 illustrates in full color typical plants of 'SOFIE' grown outdoors in Beverwijk, The Netherlands. Plants are approximately 2 years old.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'SOFIE' plants grown outdoors in Beverwijk, The Netherlands. The growing temperature ranged from approximately 1° to 12° C. at night and 10° to 25° C. during the day. Plants were described in October of 2008. Measurements and numerical values represent averages of typical flowering types. No chemical or photoperiodic treatments were given.

Botanical classification: *Symphoricarpos* hybrid cultivar 'SOFIE.'

PROPAGATION

Time to rooting: 20 days at approximately 20° C.

Root description: Fine, well branched.

PLANT

Growth habit: Perennial shrub.

Height: Approximately 79 cm.

Plant spread: Approximately 110 cm.

Growth rate: Approximately 20 cm per month.

Branching characteristics: Free branching, both basally and laterally.

Number of lateral branches: Approximately 18.

Length of lateral branches: Average 14.3 cm.

Diameter of lateral branches: Average 0.2 cm.

Texture of lateral branches: Moderately glossy.

Internode length: Approximately 2.9 cm.

Strength of stem: Flexible and strong.

Color of lateral branches: Near RHS Grey-brown N199C.

Aspect: Upright, arching outwardly.

Number of leaves per lateral branch: Average 10.

FOLIAGE

Leaf:
*Arrangement.*—Opposite, simple.
*Average length.*—Approximately 3.0 cm.
*Average width.*—Approximately 2.6 cm.
*Shape of blade.*—Broad ovate.
*Apex.*—Abruptly acute.
*Base.*—Obtuse.
*Attachment.*—Stalked.
*Margin.*—Entire, occasionally very shallowly dentate, slightly wavy.
*Texture of top surface.*—Smooth, very slightly glossy.
*Texture of bottom surface.*—Smooth.
*Leaf internode length.*—Approximately 2 cm.
*Color.*—Young foliage upper side: Near R.H.S. Green 143A. Young foliage under side: Near RHS Green143C. Mature foliage upper side: Near RHS Green N137B. Mature foliage under side: Near RHS Green to Greyed-green, in between 138B and 191A.
*Venation.*—Type: Pinnate. Venation color upper side: Near RHS Yellow-Green 148B. Venation color under side: Near RHS Yellow-Green 148C.

Petiole:
*Length.*—Average 0.3 cm.
*Diameter.*—Average 0.1 cm.
*Color.*—Near RHS Yellow-Green 144C.

FLOWER

Bloom Period: Naturally blooming July until early September in the Netherlands.
Time to flowering: First flowering begins when the plant is approximately 10 months old.
Inflorescence:
*Form.*—Single, campanulate, flowers arranged in terminal and axillary clusters.
*Quantity flowers per cluster.*—Average 14.
*Cluster size.*—Diameter: Approximately 0.4 cm. Height: Approximately 0.6 cm.
Quantity of flowers: Approximately 520 per plant.
Rate of flower opening: Approximately 3 days from bud to fully opened flower.
Flower longevity on plant: Individual flowers last 4 to 5 days on the plant.
Flower size:
*Diameter.*—Approximately 1.7 cm.
*Height.*—Approximately 2.5 cm.
Petals:
*Length.*—About 0.6 cm.
*Width.*—About 0.2 cm.
*Quantity.*—Average 5.
*Appearance.*—Dull.
*Texture.*—Under side smooth, upper side pubescent with short hairs average: 1.5 mm, colored near RHS White N155B.
*Shape.*—Broad elliptic.
*Apex.*—Broad acute.
*Base.*—Fused lower 50%.
*Margin.*—Entire.
*Aspect.*—Facing outward and slightly drooping.
*Self cleaning.*—Yes.
Color:
*When opening.*—Upper surface: Near RHS Greyed-purple 186C, upper half lighter; 186D. Lower surface: Near RHS Greyed-purple 186C.
*Fully opened.*—Upper surface: Near RHS Greyed-purple 186C, upper half lighter 186D. Lower surface: Near RHS Greyed-purple 186C. Petal color, fading to: Does not fade.

Bud:
*Shape.*—Orbicular (on top of broad ovate ovary.)
*Length.*—Approximately 0.6 cm.
*Diameter.*—Approximately 0.3 cm.
*Color.*—Near RHS Greyed-purple 185B, under side lighter 185D.

Sepals:
*Quantity per flower.*—5, fused at base.
*Arrangement.*—Funnelform.
*Shape.*—Oblong.
*Length.*—Approximately 0.3 cm.
*Width.*—Approximately 0.1 cm.
*Apex.*—Acute.
*Base.*—Fused.
*Margin.*—Entire.
*Texture.*—Pubescent.
*Appearance.*—Dull.
*Color.*—Upper Surface: Near RHS Green 143B, tips Greyed-Purple 185B. Lower Surface: Near RHS Green 143B, tips Greyed-Purple 185A.

Peduncle:
*Peduncle length.*—Approximately 1.6 cm.
*Peduncle diameter.*—Approximately 0.1 cm.
*Angle.*—Average angle of terminal peduncle: 0° (0=straight on top of lateral branch) Average angle of axillary peduncle: 60° (0=vertical).
*Color.*—Near RHS Greyed-orange 177A.
*Strength.*—Moderate.

Pedicels:
*Length.*—Approximately 0.1 cm.
*Diameter.*—Approximately 0.08 cm.
*Angle.*—Average angle 50° (0° =straight on top of peduncle).
*Strength.*—Moderate.
*Color.*—Near RHS Yellow-Green 144A.

REPRODUCTIVE ORGANS

Androecium:
*Stamens.*—Average 5.
*Anther shape.*—Dorsifixed, linear oblong.
*Anther length.*—Approximately 0.1 cm.
*Anther color.*—Near RHS Yellow 4D.
*Pollen quantity.*—Minimal.

Gynecium:
*Pistil number.*—1.
*Pistil length.*—Average 0.35 cm.
*Stigma shape.*—Club shaped.
*Style length.*—Average 0.3 cm
*Style color.*—Near RHS Green-White 157D.
*Ovary color.*—Near RHS Green 143B.

FRUIT AND SEEDS

Quantity Fruit per Plant: Average 520.
Quantity Fruit per Lateral Branch: Average 26.
Fruit Length: Average 1.3 cm.
Fruit Diameter: Average 1.4 cm.
Fruit Color: Near RHS Red-purple 70C and greyed-purple 186C, blushed lighter on underside 186D.
Fruit Texture: Smooth, moderately glossy.
Number of Days to Fruit Ripening: Average 40.

Keeping Quality: Approximately 30 days as a cut stem in a vase.
Other Fruit Characteristics: Inedible.
Quantity of Seeds per Fruit: Average 2.
Seed Shape: Flattened broad elliptic.
Seed Length: Average 0.3 cm.
Seed Diameter: Average 0.2 cm.
Seed Color: Near RHS Yellow-White 158B.

OTHER CHARACTERISTICS

Disease Resistance: Neither resistance nor susceptibility to diseases or pests has been observed in this variety.

Drought Tolerance and Cold Tolerance: Hardy perennial shrub. Tolerates high temperature to at least 32° C. Tolerates low temperatures to at least −20° C. While specific drought tolerance has not been observed, once plants are established moderate water is necessary to maintain plants.

What is claimed is:

1. A new and distinct cultivar of *Symphoricarpos* plant named 'SOFIE' as herein illustrated and described.

* * * * *